United States Patent [19]

Farfan de los Godos

[11] Patent Number: 5,647,375
[45] Date of Patent: Jul. 15, 1997

[54] METHOD AND APPARATUS FOR ASSESSING THE LUMBAR SPINE

[75] Inventor: Henry F. Farfan de los Godos, Beebe, Canada

[73] Assignee: Aurelie F. Farfan, Beebe, Canada

[21] Appl. No.: 388,849

[22] Filed: Feb. 15, 1995

[51] Int. Cl.⁶ ................................................. A61B 5/103
[52] U.S. Cl. .................................... 128/781; 128/782
[58] Field of Search ............................ 128/774, 781, 128/782; 33/511, 512

[56] References Cited

U.S. PATENT DOCUMENTS

| | | | |
|---|---|---|---|
| 5,094,249 | 3/1992 | Marras et al. | 128/781 |
| 5,337,758 | 8/1994 | Moore et al. | 128/781 |
| 5,373,858 | 12/1994 | Rose et al. | 128/782 |
| 5,462,065 | 10/1995 | Cusimano | 128/782 |
| 5,474,086 | 12/1995 | McCormick et al. | 128/782 |

*Primary Examiner*—Max Hindenburg

[57] ABSTRACT

An apparatus and a method are provided for assessing the condition of the lumbar spine of a patient. The apparatus comprises a pelvis restraint for holding the patient's pelvis fixed, a harness adapted to be secured in a fixed orientation to the patient above the lumbar spine, the harness being connected to the pelvis restraint and movable relative thereto and the harness being spring biased to a neutral position and rotatable therefrom in a first or second rotational direction against the spring biasing, and, a torque measurement device associated with the harness for measuring torque generated by the patient who twists his back in the first rotational direction and in the second rotational direction.

24 Claims, 3 Drawing Sheets

METHOD AND APPARATUS FOR ASSESSING THE LUMBAR SPINE

NATURE OF THE INVENTION

The invention relates to a method and apparatus for assessing the condition of the lumbar spine of a patient, and in particular of its torsional capability.

BACKGROUND OF THE INVENTION

The human spine is an essential load bearing component in the human skeleton. Damage to the spine may render the injured person uncomfortable, disabled or incapacitated. Any injury to the spine will likely cause at least some discomfort, immobility or pain.

Spine injuries are common. Statistics indicate that about one in every four adults suffers at some point from back or back-related problems. Many injuries of the spine occur in the lumbar region of the spine. In common everyday activities, such as lifting, sports, extended sitting, and at work, the lumbar spine is exposed to stress, and consequently to injury or re-injury. In certain activities, particularly occupational activities, stress, including torsional stress, may be repeatedly applied to the spine.

The lumbar spine can be injured in essentially two ways—namely, excessive compression or excessive torsion. If the former occurs, the most common result is a damaged vertebral end plate. The lumbar spine is relatively resistant to compression injury. The remedy is preferably rest. Corrective surgery is rarely required.

If excessive torsion or twisting occurs, the most common result is a damaged intervertebral disc. In extreme cases, the nucleus of an injured disc may rupture the annulus of the disc and protrude therethrough. Such a protruded disc, or "slipped disc" as it may colloquially be called, may pinch the spinal nerves causing extreme leg pain, or even paresis or paralysis. Corrective surgery to remove disc protrusions or even entire discs may be required. A series of relatively minor torsional injuries, if not properly identified and allowed to heal, may result in a significantly weakened disc, which may be susceptible to more serious injury. The lumbar spine is more susceptible to injury by torsion than by compression. Continued twisting toward an injured side may aggravate the injury and interfere with the healing process.

Torsion injuries can occur independently in the two rotational directions.

Some injuries can, of course, involve some combination of the above basic injury modes.

If a patient complains of back pain, it is critical that a proper diagnosis or assessment of the spine be made in order to determine whether there has been any injury to the lumbar spine and, if so, the nature and extent of the injury. Depending on the true nature of any injury, then different treatment regimens will be prescribed. The problem is that, practically speaking, it can very difficult for a medical practitioner to assess the condition of the lumbar spine and the precise nature of the injury. Very few tools are available to assist the medical practitioner in conducting the assessment.

STATEMENT OF THE INVENTION

With a view to overcoming the foregoing problems, the invention comprises an apparatus for assessing the condition of the lumbar spine of a patient comprising a pelvis restraint for holding the patient's pelvis fixed, a harness adapted to be secured in a fixed orientation to the patient above the lumbar spine, the harness being connected to the pelvis restraint and movable relative thereto and the harness being spring biased to a neutral position and rotatable therefrom in a first or second rotational direction against the spring biasing, and, torque measuring means associated with the harness for measuring torque generated by a patient who twists his back in the first rotational direction and in the second rotational direction.

In another embodiment, the invention is a method for assessing the condition of the lumbar spine of a patient comprising measuring the maximum torque the patient is capable of generating by twisting his back in a first rotational direction, measuring the maximum torque the patient is capable of generating by twisting his back in a second rotational direction, and, comparing the two measurements in a first comparison.

BRIEF DESCRIPTION OF THE DRAWINGS

The above as well as other advantages and features of the present invention will be described in greater detail according to the preferred embodiments in which.

DESCRIPTION OF A DETAILED EMBODIMENT

Figure 1:
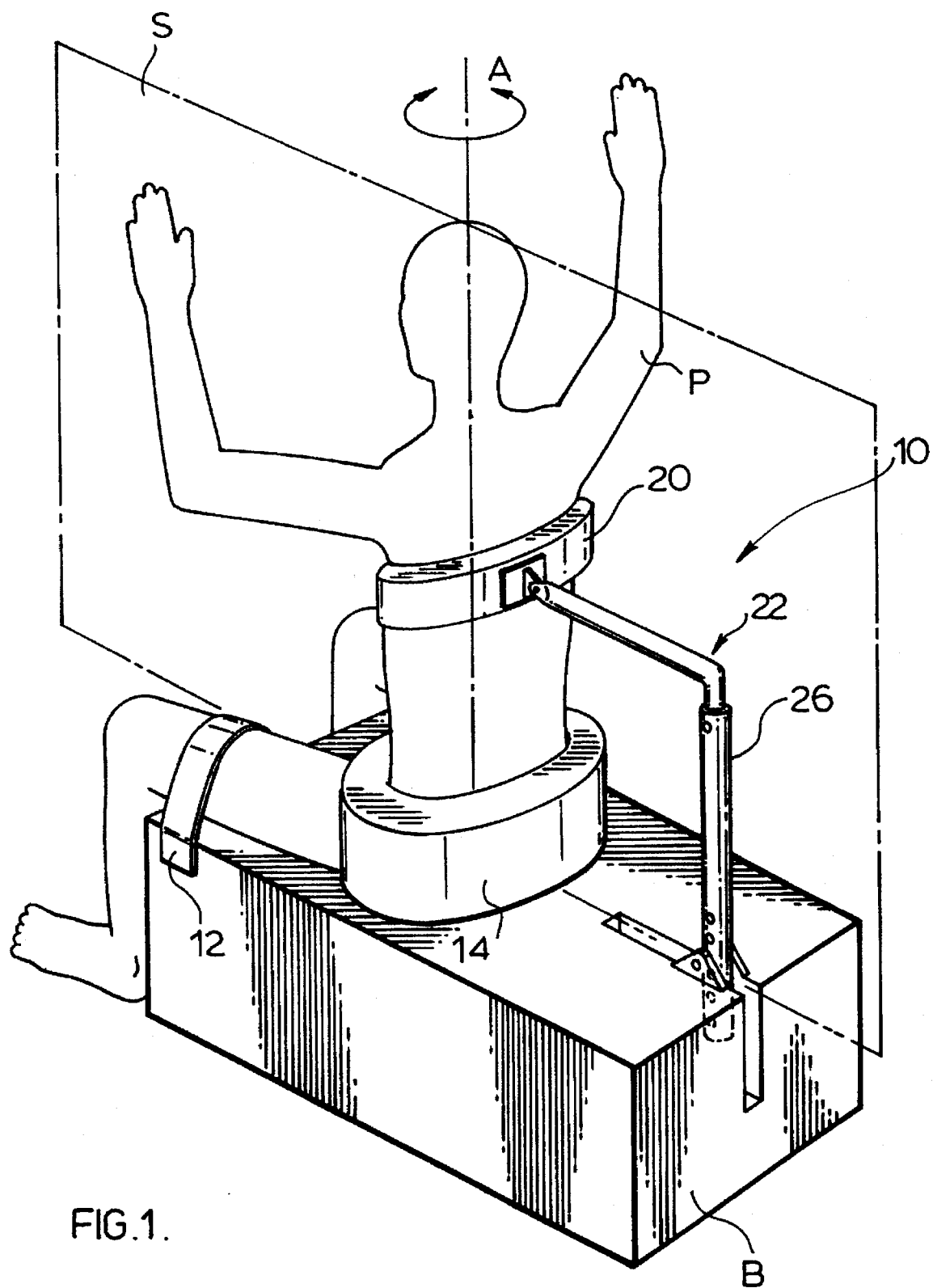
FIG. 1 shows the apparatus according to one embodiment of the invention attached to a patient.

Referring to FIG. 1, patient P is shown in seated position. An assessment apparatus according to the invention is generally indicated as 10 and is attached to the patient P and to base B. The patient's legs are restrained by restraints 12 to base B. The patient's pelvis is firmly held in a pelvis restraining means 14 which prevents rotation or other movement of the pelvis during the assessment procedure.

Figure 4:
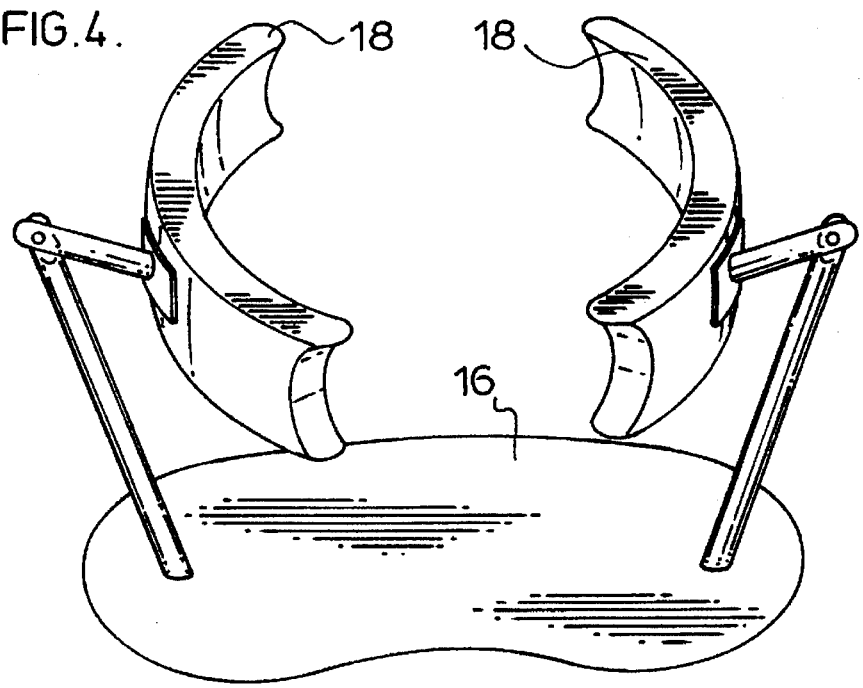
FIG. 4 shows an alternate embodiment of the pelvis restraining means according to the invention.

In another embodiment as shown in FIG. 4, pelvis restraining means 14 could comprise a seat 16 and adjustable hip clamps 18 which could be locked into place about the patient's hips. Other arrangements could be used as well.

A harness 20 is worn by patient P. It is snugly fixed to his torso above the lumbar spine, preferably at about the level of the patient's thoracic vertebrae T6 to T10. It is sufficiently tight that the patient's torso cannot move relative to harness 20 during the assessment procedure.

Harness 20 is connected, through linkage means 22 and base B, to the pelvis restraining means 14 but is rotatable relative thereto in both first and second rotational directions. It is biased in spring-like manner to be held normally in a neutral position, preferably transverse to the sagittal plane S. The spring-like biasing may be achieved in any manner, including by the use of various springs or other resilient means. In the illustrated embodiment, as described below, the biasing is achieved by the natural elasticity of a rod 26 to which torque is applied.

Figure 3:
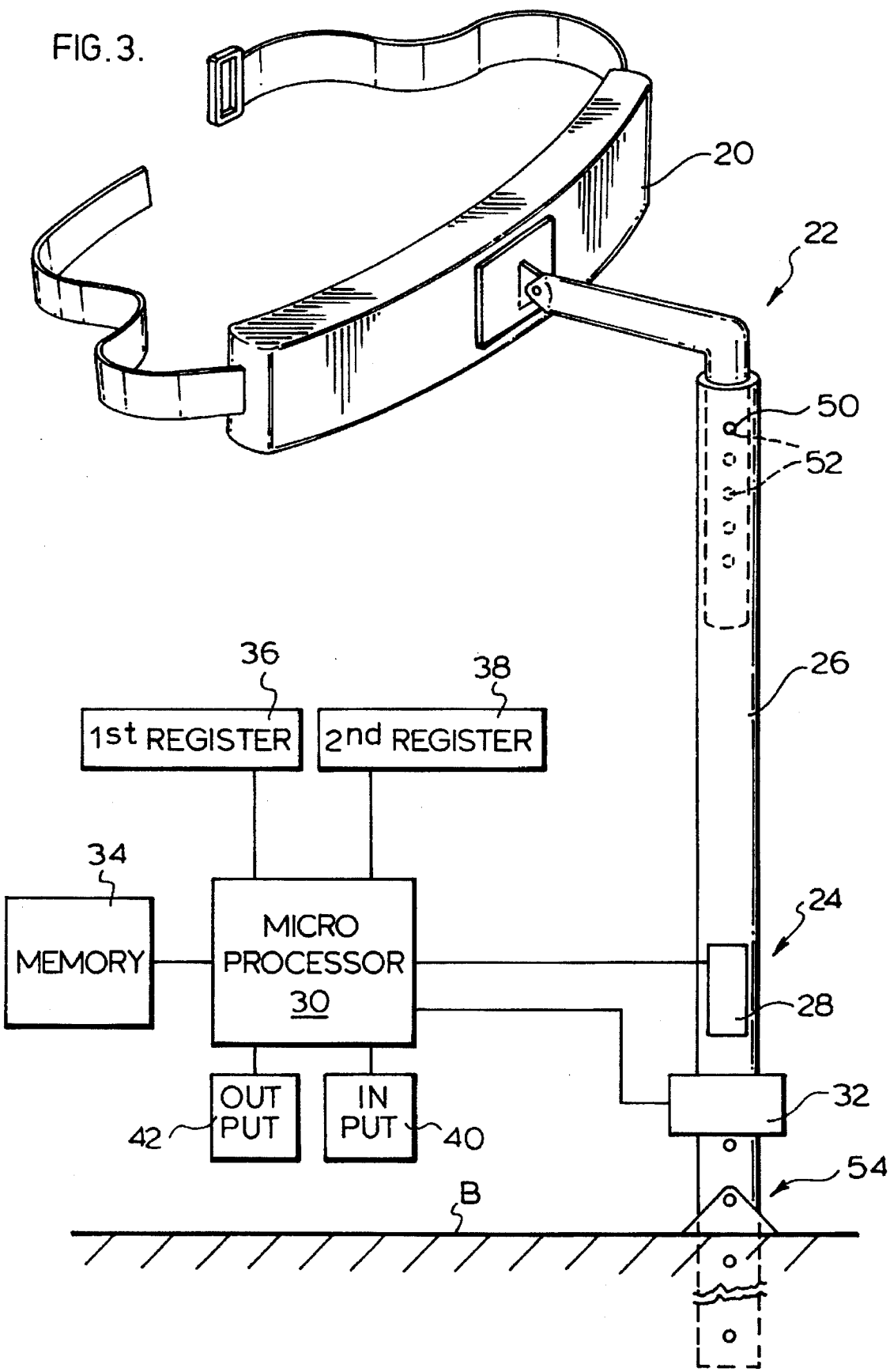
FIG. 3 shows the apparatus according to one embodiment of the invention.

Referring to FIG. 3, the connection between harness 20 and pelvis restraining means 14 is through an adjustable linkage means 22. Linkage means 22 is adjustable by any suitable adjustment means, for example pin 50 through holes 52, to accommodate patients of different height.

Torque measuring means 24 is associated with harness 20 and functions to measure the torque generated by patient P when twisting about axis A in either rotational direction.

In the particular embodiment shown in FIG. 3, linkage means 22 includes a torque rod 26 positioned in the sagittal plane S, preferably some distance away from the patient's back, for reasons noted below. Mounted to torque rod 26 is torque measurement device 28, which could for example include strain gauge transducers.

Preferably, torsion measurement means 28 operates electronically, whereby measurements are automatically digitized for processing in a microprocessor 30. However, in other embodiments, torque measurements could be read from mechanical or other devices.

Input and output devices 40 and 42 are provided for transfer of data to and from microprocessor 30. A memory means 34 is provided for storing predetermined standard values for patients in good health against which the results of the tests on patient P can be compared. Said standard values can be arranged by certain physical characteristics such as age and sex. These standard values should at least include standard torsion values, but may also include standard minimum and maximum flexion values as well. Memory means 34 may also store torsion and flexion values as associated with various spine conditions. For example, good torsion and good flexion suggest a healthy spine. Good torsion and bad flexion may suggest osteoarthritis of the lumbar spine. Moderately poor torsion and good flexion may suggest the presence of an early torsion injury. Poor torsion and poor flexion may suggest the presence of a significant torsion injury.

It may be preferable that some of the various predetermined standard values be normalized for certain physical characteristics, such as body weight.

Figure 2:
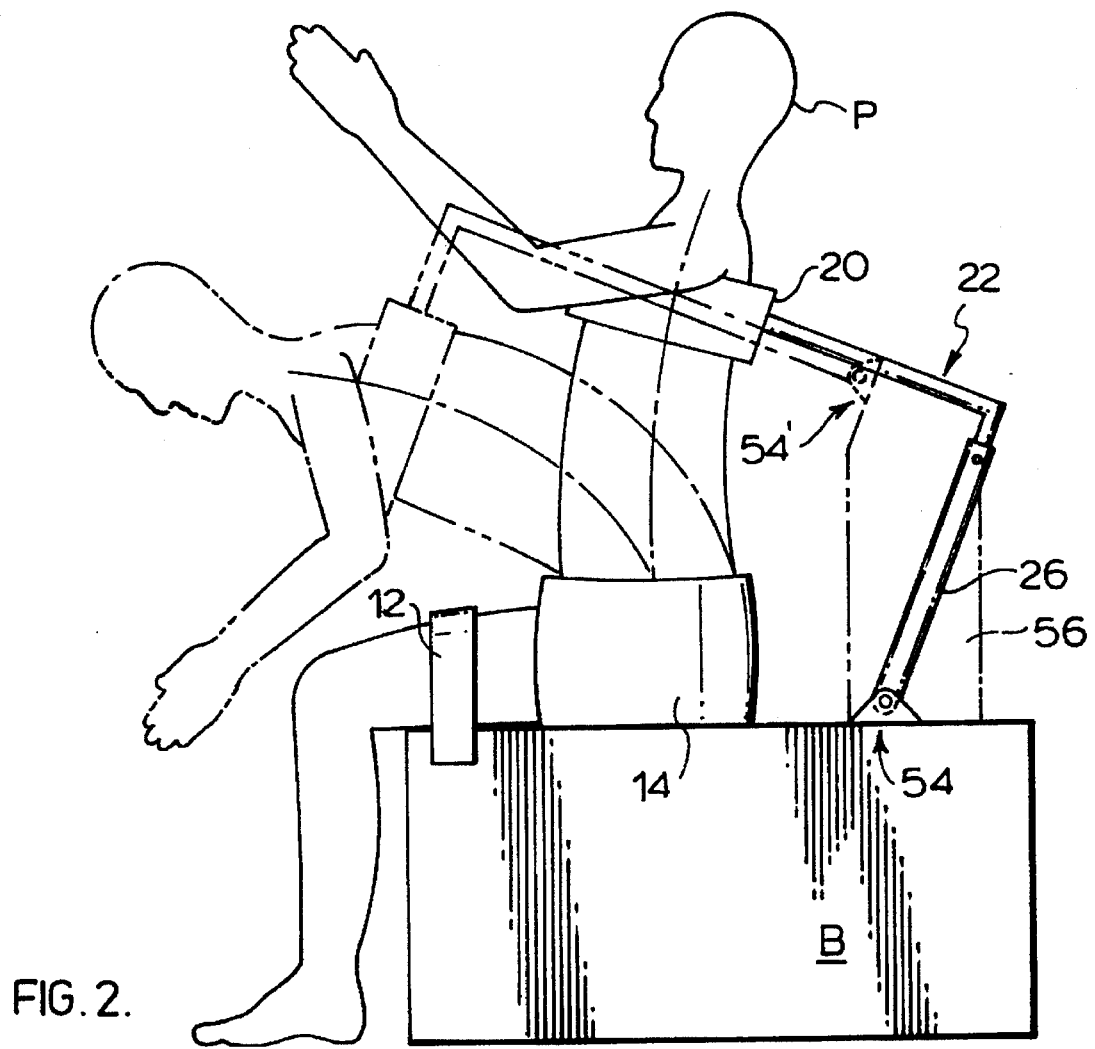
FIG. 2 is a side view of the apparatus according to one embodiment of the invention attached to a patient.

In a preferred embodiment, apparatus 10 is also adjustable to accommodate the taking of torque measurements in a patient at different degrees of spinal flexion, as shown for example in FIG. 2 which illustrates patient P in two different positions—i.e. an upright fully extended position (solid lines, representing about 0° of flexion) and a bent over fully flexed position (dashed lines, representing about 60° of flexion). An angle measuring device 32, such as an inclinometer, is provided for the purpose of measuring the patient's flexion position.

To allow the necessary flexion, torque rod 26 is pivotally and detachably mounted to the base B at pivot 54. In addition, the position of pivot 54 must be adjustable relative to base B. Base extension block 56 is adaptable to be attached to base B and to receive and hold pivot 54' at any appropriate point.

Having the torque rod 26 positioned some distance away from the patient's back, in conjunction with the base extension block 56 if necessary, allows patient P to flex between the fully extended and the fully flexed position without interference by rod 26.

In operation, the relevant physical characteristics of patient P (e.g. age, sex, body weight) are inputted to the microprocessor 30 via input means 40. The patient's hips are secured in pelvic restraint means 14 and his legs in leg restraints 12. Linkage means 22 is adjusted to a comfortable position for the patient's height and harness 20 fixed in place about the patient's torso, as noted preferably between about T6 and T10. Patient P then twists his torso in a first rotational direction as far as he can. Torque sensor device 28 measures the maximum torque generated by patient P in undertaking that activity. Processor 30 stores a value representing the measured torque in a first measurement register 36. Patient P then twists in the opposite direction, i.e. the second rotational direction, to generate a second maximum torque measurement which is stored by processor 30 in a second register 38.

The torque values in each direction are then compared in a first comparison to each other, preferably automatically in microprocessor 30, resulting in a difference signal. If normalized standard values are used, the difference signal is normalized for the patient's relevant characteristics (e.g. body weight).

The difference signal or normalized difference signal, as the case may be, is then compared in a second comparison to predetermined standard values for patients in good health having similar pre-determined physical characteristics (e.g. sex and age) to determine whether the difference is within normal ranges. If the difference is not within the normal range, then the rotational direction in which the torque value was less can reasonably be ascribed as having a possible torsional injury in that same rotational direction. An appropriate torsion assessment signal is generated by microprocessor 30.

Processor 30 can supply an appropriate torsion assessment report by the output means 42.

Preferably, a number of measurements can be taken as patient P repeats the above steps. The values for all such tests can be averaged.

In addition, in a more comprehensive test, the same patient P can repeat the above steps at different flexion angles, for example at 30° and at a fully flexed position at about 60°. Each of these tests can be compared against the predetermined standards for patients in good health at corresponding flexion angles.

Furthermore, a test of the patient's minimum and maximum flexion positions can be performed and the results compared in a third comparison to the standard flexion values for patients in good health. A flexion assessment signal can be generated and a report can be provided accordingly at output means 42.

In addition, the torsion and flexion assessment signals can, as a pair, be compared in a fourth comparison against a pre-determined table or set of torsion and flexion values associated with various spine conditions stored in memory means 34. A spine condition signal can be generated and a report can be provided accordingly at output means 42.

Although various preferred embodiments of the present invention have been described herein in detail, it will be appreciated by those skilled in the art, that variations may be made thereto without departing from the spirit of the invention or the scope of the appended claims.

I claim:

1. An apparatus for assessing the condition of the lumbar spine of a patient comprising:

a pelvis restraining means for holding the patient's pelvis fixed;

a harness adapted to be secured in a fixed orientation to the patient above the lumbar spine, said harness being connected to said pelvis restraining means and movable relative thereto and said harness being spring biased to a neutral position and rotatable therefrom in a first or second rotational direction against said spring biasing whereby force applied by said spring biasing increases with annular displacement from the neutral position; and, torque measuring means associated with said harness for measuring torque generated by a patient who twists his back in the first rotational direction and in the second rotational direction against said spring biasing.

2. An apparatus as claimed in claim 1 wherein said apparatus further comprises angle measurement means for measuring the angle of a patient's flexion position.

3. An apparatus as claimed in claim 1 wherein said apparatus further comprises:

processing means for firstly comparing the torques generated in said two directions, for generating a difference signal indicative of the difference therebetween, for secondly comparing said signal to a first pre-determined threshold value and for generating a torsion assessment signal in response to said second comparison.

4. An apparatus as claimed in claim 3 wherein said apparatus further comprises:

input means connected to said processing means for inputting data relating to pre-determined physical characteristics of the patient, and, memory means connected to said processing means for storing standard threshold values according to at least one of said pre-determined physical characteristics, and wherein said first pre-determined threshold value is selected from said memory means according to the corresponding at least one of said pre-determined physical characteristics of the patient.

5. An apparatus as claimed in claim 4 wherein said apparatus further comprises angle measurement means for measuring the angle of a patient's flexion position.

6. An apparatus as claimed in claim 5 wherein said memory means stores said standard threshold values for various flexion positions and said pre-determined threshold value is also selected according to a patient's flexion position.

7. An apparatus as claimed in claim 6 wherein said processing means additionally is for thirdly comparing a patient's minimum and maximum flexion positions with second pre-determined threshold values, selected from said memory means according to the corresponding at least one of said pre-determined physical characteristics of the patient, and for generating a flexion assessment signal in response to said third comparisons.

8. An apparatus as claimed in claim 7 wherein said processing means additionally is for fourthly comparing the torsion assessment signal and the flexion assessment signal, as a pair, to a pre-determined set of torsion and flexion values associated various spine conditions and for generating a spine condition signal in response to said fourth comparison.

9. An apparatus as claimed in claim 4 wherein said difference signal is normalized for at least one pre-determined physical characteristic of the patient and said standard threshold values are correspondingly normalized.

10. An apparatus as claimed in claim 9 wherein said at least one pre-determined physical characteristic is body weight.

11. An apparatus as claimed in claim 3 wherein said harness is connected to the pelvis restraining means by a torque rod and said torque measuring means comprises torque measurement means attached to said torque rod for measuring torque applied thereto.

12. An apparatus as claimed in claim 11 wherein said torque measurement means comprises strain gauge measurement means.

13. A method for assessing the condition of the lumbar spine of a patient comprising:

measuring the maximum torque the patient is capable of generating by twisting his back in a first rotational direction;

measuring the maximum torque the patient is capable of generating by twisting his back in a second rotational direction; and, comparing the two measurements in a first comparison.

14. A method as claimed in claim 13 wherein:

said twisting in said first direction is from a neutral position and is against a spring biasing force which increases with angular displacement from the neutral position; and, said twisting in said second direction is also from said neutral position and is against a spring biasing force which increases with angular displacement from the neutral position.

15. A method as claimed in claim 14 further comprising measuring the angle of a patient's flexion position.

16. A method as claimed in claim 14 further comprising:

generating a difference signal indicative of the result of the first comparison;

comparing in a second comparison said signal to a first pre-determined threshold value; and, generating a torsion assessment signal in response to said second comparison.

17. A method as claimed in claim 16 further comprising:

selecting said first pre-determined threshold value from a pre-determined set of standard threshold values according to at least one of said pre-determined physical characteristics of the patient.

18. A method as claimed in claim 17 further comprising measuring the patient's flexion angle.

19. A method as claimed in claim 18 wherein said selecting of said pre-determined threshold value is also selected according to a patient's flexion position.

20. A method as claimed in claim 19 further comprising comparing in a third comparison a patient's minimum and maximum flexion positions with second pre-determined threshold values, selected according to the corresponding at least one of said pre-determined physical characteristics of the patient, and generating a flexion assessment signal in response to said third comparisons.

21. A method as claimed in claim 20 further comprising comparing in a fourth comparison the torsion assessment signal and the flexion assessment signal, as a pair, to a pre-determined set of torsion and flexion values associated various spine conditions and generating a spine condition signal in response to said fourth comparison.

22. A method as claimed in claim 17 wherein said difference signal is normalized for at least one pre-determined physical characteristic of the patient and said standard threshold values are correspondingly normalized.

23. A method as claimed in claim 22 wherein said at least one pre-determined physical characteristic is body weight.

24. An apparatus for assessing the condition of the lumbar spine of a patient comprising:

torque measuring means for measuring the maximum torque generated by the patient who twists his back in a first rotational direction and for measuring the maximum torque generated by the patient who twists his back in a second rotational direction;

means for comparing the two torque measurements in a first comparison.

* * * * *